(12) United States Patent
Valaskovic

(10) Patent No.: US 6,690,006 B2
(45) Date of Patent: Feb. 10, 2004

(54) METHOD AND APPARATUS FOR MULTIPLE ELECTROSPRAY SAMPLE INTRODUCTION

(75) Inventor: Gary A. Valaskovic, Cambridge, MA (US)

(73) Assignee: New Objective, Inc., Woburn, MA (US)

(*) Notice: Subject to any disclaimer, the term of this patent is extended or adjusted under 35 U.S.C. 154(b) by 0 days.

(21) Appl. No.: 10/155,646

(22) Filed: May 23, 2002

(65) Prior Publication Data

US 2002/0175281 A1 Nov. 28, 2002

Related U.S. Application Data

(60) Provisional application No. 60/293,282, filed on May 24, 2001.

(51) Int. Cl.[7] .............................................. B01D 59/44
(52) U.S. Cl. ...................................................... 250/288
(58) Field of Search ........................................ 250/288

(56) References Cited

U.S. PATENT DOCUMENTS

| | | | |
|---|---|---|---|
| 4,977,785 A | 12/1990 | Willoughby et al. | |
| 5,423,964 A | 6/1995 | Smith et al. | |
| 5,917,184 A | 6/1999 | Carson et al. | |
| 6,025,591 A | 2/2000 | Taylor et al. | 250/292 |
| 6,191,418 B1 | 2/2001 | Hindsgaul et al. | 250/288 |
| 6,207,954 B1 * | 3/2001 | Andrien et al. | 250/288 |
| 6,207,955 B1 | 3/2001 | Wells et al. | |
| 6,239,429 B1 | 5/2001 | Blessing et al. | 250/292 |
| 6,271,527 B1 | 8/2001 | Chutjian et al. | 250/427 |
| 6,297,499 B1 * | 10/2001 | Fenn | 250/288 |
| 6,326,616 B1 | 12/2001 | Andrien, Jr. et al. | |
| 6,350,617 B1 | 2/2002 | Hindsgaul et al. | 436/173 |
| 6,410,915 B1 | 6/2002 | Bateman et al. | |
| 6,437,327 B2 * | 8/2002 | Takada et al. | 250/288 |
| 2001/0013579 A1 | 8/2001 | Andrien, Jr. et al. | 250/423 |
| 2001/0020678 A1 | 9/2001 | Hindsgual et al. | 250/288 |
| 2001/0042828 A1 | 11/2001 | Hindsgual et al. | 250/288 |
| 2002/0000516 A1 | 1/2002 | Schultz et al. | 250/288 |
| 2002/0000517 A1 | 1/2002 | Corso et al. | 250/288 |
| 2002/0003177 A1 | 1/2002 | O'Connor et al | |
| 2002/0005480 A1 | 1/2002 | Harada | 250/288 |
| 2002/0027197 A1 | 3/2002 | Duholke et al. | 250/288 |

* cited by examiner

Primary Examiner—John R. Lee
Assistant Examiner—Johnnie L Smith, II
(74) Attorney, Agent, or Firm—Norris McLaughlin & Marcus

(57) ABSTRACT

A method for the coupling of a plurality of sample streams eluting from a plurality of High Pressure Liquid Chromatography columns into a single inlet mass spectrometer, wherein samples from individual chromatography columns are suppled to individual electrospray nozzles in an array of a plurality of electrospray nozzles positioned in front of said single inlet, each nozzle being switchable to an on or off state, and each nozzle being supplied by a sample supply tube or channel and having, in addition to said sample supply tube or channel, a separate fluid removal tube or channel, and wherein each nozzle, when in the off state, is held at a voltage that is between the voltage of the mass spectrometer inlet and the electrospray threshold value for that nozzle.

1 Claim, 3 Drawing Sheets

Cross Section View                Front End View

METHOD AND APPARATUS FOR MULTIPLE ELECTROSPRAY SAMPLE INTRODUCTION

This application claims the benefit of provisional application no. 60/293,282 filed on May 24, 2001.

This invention pertains to the field of analytical chemistry. More particularly, the invention pertains to liquid chromatography in combination with electrospray ionization mass spectrometry. In accordance with the method of the present invention, a plurality of sample streams eluting from a plurality of HPLC (High Pressure Liquid Chromatography) columns are coupled into a single inlet mass spectrometer.

BACKGROUND OF THE INVENTION

It is known in the prior art to create multiple (array) nozzles for electrospray ionization. The known methods, in general, utilize one of three techniques for achieving separate signals from multiple spray nozzles. In one known method, the inlet is translated with respect to the nozzle "array" while all of the nozzles spray simultaneously. In a second known method, the electrospray high voltage is switched on and off on each nozzle. In yet a third method, a mass spectrometer with multiple nozzles is used, each nozzle having a separate inlet. In some cases, a combination of at least two of the foregoing methods is used.

Andren et. al., in Proceedings for the 46$^{th}$ ASMS Conference on Mass Spectrometry and Allied Topics, Page 889, 1998, discloses a method utilizing a multiple probe spray source with two fixed spray nozzles. Each nozzle voltage can be turned on or off independently. A primary nozzle was configured to spray "head on" into the inlet. The secondary nozzle was fixed at an angle of 60° to the first. The two nozzles were separated by a moderate distance. This method corresponds to the second method discussed above.

Jiang & Moini, in Analytical Chemistry 72, 20–24, 2000, disclose a multiple inlet source in which four independent spray nozzles are each provided with a separate inlet (sampling orifice) into a mass spectrometer. Spectra are obtained from the four nozzles simultaneously. This corresponds to the third method discussed above.

Hannis & Muddiman, in Journal of the American Society for Mass Spectrometry 11, 876–883, 2000, disclose a two-nozzle interface that sequentially moves each nozzle in front of a mass spectrometer inlet by electromechanical means. This corresponds to the first method discussed above.

Karger et al. U.S. Pat. No. 5,872,010, discloses an array of nozzles on a chip-based device. The nozzles are switched in voltage and translated in front of a single mass spectrometer inlet. This corresponds to a combination of the first and second methods discussed above.

Kassel et al. U.S. Pat. No. 6,066,848 discloses a linear array of nozzles in front of a single inlet. A screen device which blocks the signal from all but one of the nozzles is placed between the array and the inlet. By electromechanically translating the screen, signal from each of the nozzles can be obtained sequentially. All of the nozzles remain operational, i.e., "on", throughout the procedure.

None of the foregoing methods is completely satisfactory, however, especially where high sensitivity is required.

SUMMARY OF THE INVENTION

In accordance with the present invention, an array of a plurality of nozzles, either linear or two-dimensional, is positioned in front of the inlet of an electrospray ionization mass spectrometer. Samples for analysis are delivered through each nozzle, using known pumping systems.

The nozzles, in accordance with the present invention, when in an "off" mode, are held at a fractional voltage, which is between the electrical potential of the mass spectrometer inlet and the electrospray threshold value. In addition, each nozzle of the present invention is provided with a integral fluid removal tube or channel, which is separate from the channel that delivers sample material to the nozzle.

The fractional voltage enables the nozzles to be located in close proximity to each other by minimizing or eliminating the effect of the electric field of an "on" nozzle on an adjacent "off" nozzle; and the separate integral fluid removal tube or channel provided to each nozzle enables a capillary wicking or the application of a vacuum suction to remove excess fluid from the nozzles.

DETAILED DESCRIPTION

In the method of the present invention, an array of a plurality of nozzles, which can be either linear or two-dimensional, is positioned in front of the inlet of an electrospray ionization mass spectrometer. Each of the nozzles is provided with or operated in accordance with the following two features:

In the first feature, the voltage suppled to a given nozzle is not simply switched from "on" when charging samples to the mass spectrometer to "off" at the completion of the sample charge, as in the prior art. Instead, upon completion of the charge of the sample from the nozzle to the mass spectrometer, the voltage applied between the nozzle and the inlet system to the mass spectrometer, for a nozzle in the "off" position, is adjusted to a value that is below the electrospray threshold voltage, but above the voltage applied to the inlet to the mass spectrometer. As a result of this voltage adjustment, the generation of ion current, or signal, that would otherwise be generated in the nozzle is minimized or eliminated.

The "electrospray threshold voltage" is the minimum voltage at which an electrostatically generated spray with a stable cone (known as a "Taylor Cone") is formed. This is also known in the art as the "cone jet" mode. At a voltage slightly below the threshold voltage, i.e., within about 10% below the threshold voltage, transient sprays can be formed and/or large droplets which "spit" from the end of the nozzle can be formed. At voltages which are more than about 10% below the threshold voltage, no droplets are generated.

Thus, when a nozzle is in the "off" position, in accordance with the present invention, the voltage is set at a value at which the electrostatic attraction of the liquid to the counter-electrode is unable to overcome the surface tension holding the liquid together at the end of the nozzle, and therefore no liquid (droplets or spray) emits from the nozzle.

In the prior art, when a nozzle that was in an "off" mode located in close proximity to a nozzle that was in the "on" mode, was allowed to float at an unspecified voltage, fluid remaining in the nozzle that was in the "off" mode could be affected by an electrical field generated by the "on" nozzle and be induced into a temporary "on" state. As a result of this, the mass spectrometer could obtain signals from more than one nozzle at the same time. This problem in the prior art limits the ultimate packing density of nozzles placed in front of a mass spectrometer inlet. In order to eliminate the induction of signal in a nozzle that is in the off mode from an adjacent nozzle that is in the "on" mode, the individual nozzles of the prior art must be spaced further apart from each other than would otherwise be desirable.

Alternatively, the voltage of an "off" nozzle was held at ground, or at a potential close to that of the mass spectrometer inlet in the prior art. In this case, the electrical field surrounding an "on" nozzle could generate ions which are then attracted to a nearby "off" nozzle. In order to minimize or eliminate this effect, the nozzles have to be spaced apart from each other a greater distance than would otherwise be desirable.

In addition, the phenomenon described above could, in the prior art, cause chemical contamination of the "off" nozzles with fluid from the "on" nozzles.

By using the method of the present invention, wherein the "off" nozzles are held at a factional voltage, which is between the electrical potential of the mass spectrometer inlet and that of the electrospray threshold value, the nozzles are able to be placed in closer proximity to each other than has heretofore been possible, while minimizing or eliminating the above-described induction of transient signals between nozzles.

In a second aspect of the present invention, each nozzle is provided with an integral fluid removal tube or channel, which is separate from the channel or tube through which sample fluids are supplied to the nozzle. This fluid removal tube or channel provides a capillary wicking or active vacuum suction to remove excess fluid from the nozzle. The action of the fluid removal tube or channel is switchable between being active (on) or inactive (off). Thus, when a nozzle is brought below the electrospray threshold voltage, the action of the fluid removal channel is turned on to remove any fluid that remains in or continues to flow through that nozzle. By doing this, such remaining fluid is prevented from accumulating at the tip of the "off" nozzle. This, in turn, minimizes or eliminates the prior art difficulties wherein excess fluid would accumulate at a nozzle end, and swamp the nozzle array. This swamping, in turn, leads to unstable signals in the prior art, if the accumulated excess fluid comes in contact with an "on" nozzle; and also can lead to cross-contamination of the samples in the nozzle array. In addition, the removal of excess fluid from the "off" nozzles, in accordance with the present invention, provides for a rapid stabilizing of a nozzle when switched from the off state to the on state.

Figure 1:
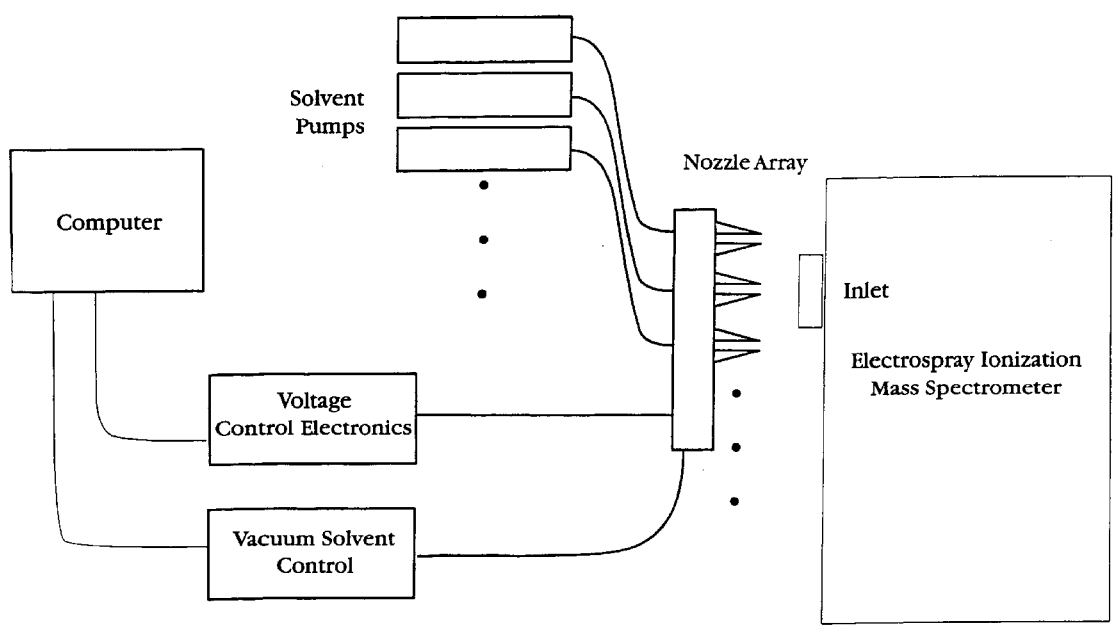
FIG. 1 is a schematic illustrating a system used in the practice of the present invention.
Figure 2:
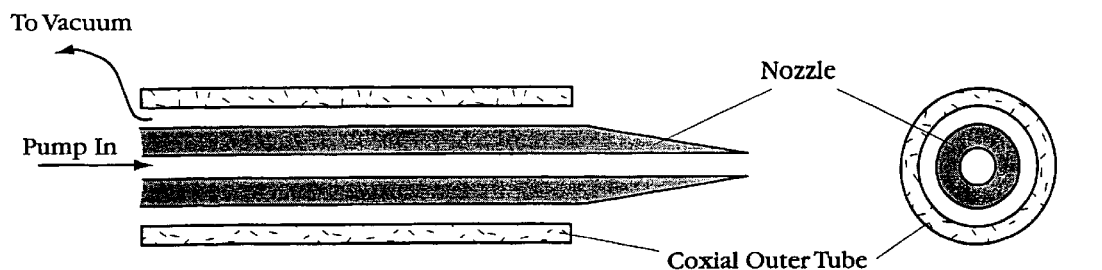
FIG. 2 depicts a coaxial tube arrangement according to the invention.
Figure 3:
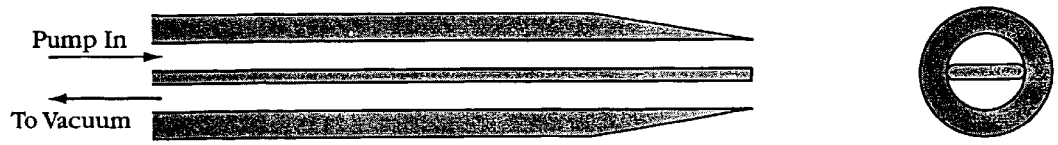
FIG. 3 depicts a parallel, multi-lumen arrangement, with an equal limen design according to the invention.
Figure 4:
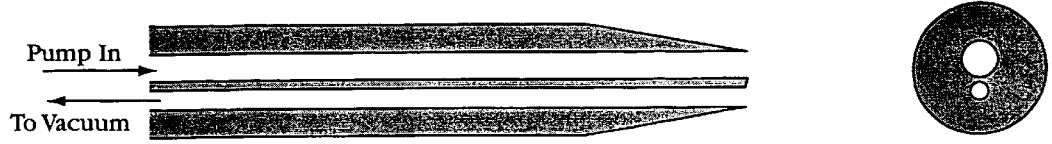
FIG. 4 depicts a parallel, multi-lumen arrangement with an unequal lumen design according to the invention.
Figure 5:
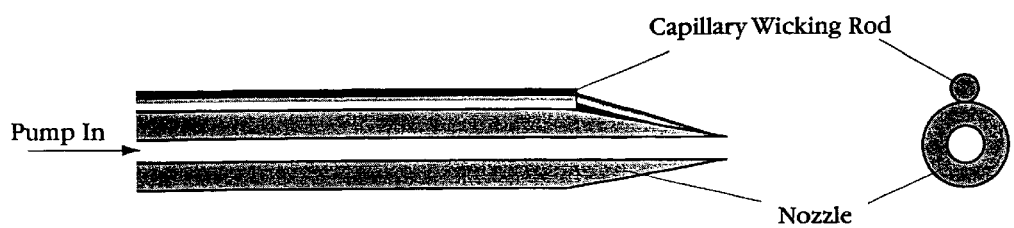
FIG. 5 depicts a capillary wicking design according to the invention.
Figure 6:
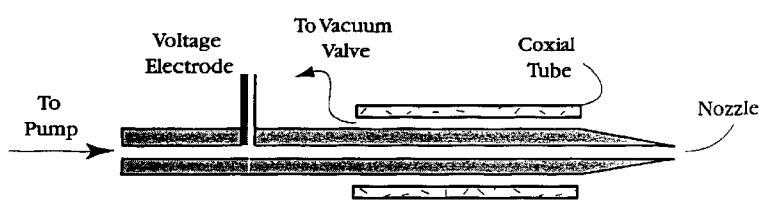
FIG. 6 is a schematic if the coaxial nozzle design utilizing a wire electrode in a junction for voltage contact.

Although not shown, the nozzle could be constructed of a material that is electrically conductive or the nozzle could have an electrically conductive coating applied to its outside surface, in addition to or instead of using the junction style contact shown in FIG. 6.

Figure 7:
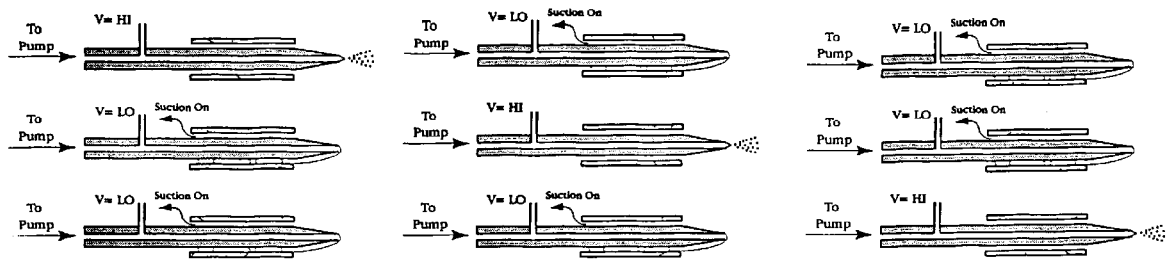

FIG. 7 depicts the sequential operation of a 3-nozzle array of the coaxial tube design.

EXAMPLE

An array of two electrospray nozzles was constructed from tapered fused silica tubing (360 $\mu$m OD×75 $\mu$m ID, tapered to a 30 $\mu$m OD tip). Each nozzle was placed through a coaxial tube of larger diameter (ID and OD) to form a coaxial channel in between the inner fused silica tubing and the outer (sheath) tube. This coaxial channel creates a second channel, for sample removal. Each nozzle in turn was connected to an electromechanical solenoid valve connected to a vacuum source. The solenoid valve was connected to a computer-controlled interface system. The tapered nozzle protruded beyond the end of the sheath tubing by approximately 1–2 mm.

The distal end of each fused silica nozzle was connected to a mobile phase delivery system (pump) via a transfer line. At the connection point, a platinum electrode was placed to provide the electrical potential necessary for electrospray. Each electrode was attached to the output of a variable potential high voltage power supply. The voltage controller of the power supply was connected to a computer controlled interface system.

The computer system was programmed to alter the voltage applied to each nozzle assembly at the same time that the solenoid valve was switched. When a nozzle was turned on, the suction to that nozzle was turned off; when a nozzle was turned off, the suction to that nozzle was turned on.

The two 30 $\mu$m ID nozzles were placed in close proximity (0.3 to 0.4 mm) to each other. The nozzles were also placed very close to the mass spectrometer inlet (approximately 1–2 mm). The electrospray threshold voltage for the nozzles was determined to be 1500 volts, and the "on" voltage was set to 1800 volts. An "off" nozzle voltage that did not cause electrospray in the "off" nozzle, while at the same time allowing for minimal signal loss from the "on" nozzle to the "off" nozzle was found to be in the range of from about 500 to about 800 volts. The "off" nozzle voltage was then set at 600 volts.

A sample of biologically derived peptide was dissolved in a 50% mixture of acetonitrile/water in 0.1% formic acid to yield a concentration of approximately 1 micromole of the peptide per liter of solution. This solution was supplied to each of the two nozzles. Approximately equal mass-selected ion currents, i.e., within about 10% of each other, were obtained from the two nozzles.

I claim:

1. A method for the coupling of a plurality of sample streams eluting from a plurality of High Pressure Liquid Chromatography columns into a single inlet mass spectrometer, wherein samples from individual chromatography columns are supplied to individual electrospray nozzles in an array of a plurality of electrospray nozzles positioned in front of said single inlet, each nozzle being switchable to an on or off state, and each nozzle being supplied by a sample supply tube or channel and having, in addition to said sample supply tube or channel, a separate fluid removal tube or channel, and wherein each nozzle, when in the off state, is held at a voltage that is between the voltage of the mass spectrometer inlet and the electrospray threshold value for that nozzle.

* * * * *